United States Patent [19]

Hayes et al.

[11] 4,423,030
[45] Dec. 27, 1983

[54] FLAVORED AQUEOUS ORAL COMPOSITION

[75] Inventors: Harry Hayes, Warrington; Munir A. Ahmed, Firswood, both of England

[73] Assignee: Colgate-Palmolive Company, New York, N.Y.

[21] Appl. No.: 375,783

[22] Filed: May 6, 1982

[30] Foreign Application Priority Data

May 13, 1981 [GB] United Kingdom ............... 81145066

[51] Int. Cl.³ .................. A61K 7/16; A61K 7/26; A61K 35/78
[52] U.S. Cl. ........................... 424/58; 424/10; 424/48; 424/49; 424/195; 426/3; 426/534; 426/638; 426/651
[58] Field of Search .................. 424/48–58, 424/10, 195; 426/3, 534, 651

[56] References Cited

U.S. PATENT DOCUMENTS

| 1,381,282 | 8/1921 | Green | 424/58 |
| 1,488,097 | 3/1924 | Creger | 424/58 |
| 3,720,762 | 3/1973 | Hatasa | 424/58 |
| 3,947,570 | 3/1976 | Pensak | 424/58 |
| 4,060,602 | 11/1977 | Haas et al. | 424/58 |
| 4,071,614 | 1/1978 | Grimm | 424/58 |
| 4,132,770 | 1/1979 | Barth | 424/58 |
| 4,216,200 | 8/1980 | Horn | 424/58 |
| 4,242,323 | 12/1980 | Vlock | 424/58 |
| 4,272,513 | 6/1981 | Gaffar | 424/58 |

FOREIGN PATENT DOCUMENTS

| 2369845 | 7/1978 | France | 424/58 |
| 57-38708 | 3/1982 | Japan | 424/58 |
| 1438205 | 6/1976 | United Kingdom . | |

OTHER PUBLICATIONS

Jacobs "How to Flavor Toothpaste" Flavoring Mouthwashes Am. Perf. & Essential Oil Review 61: 389 391 393 May 1953, 469 471 Jun. 1953.
Steffen Artander Perfume and Flavor Materials of Natural Origin (1960) columns 67 Anise Anethole 241, Fennel Oil Sweet Anethole 225–236 Eucalyptus 513 Peppermint Menthol 122–123 Capsicum Oleoresin 518–519 Black Pepper Oleoresin 279–281 Ginger Oleoresin 199 Cubeb Oleoresin 200–201 Cumin Oleoresin.
Fritzche, Dodge & Olcott, Inc. New York, N.Y. "The Oleoresin Handbook" 2nd Ed. May 1974.
Fenaroli's Handbook of Flavor Ingredients 2nd Ed. (1975) CRC Press, Cleveland, Ohio, U.S.A. pp. 304–306, 364–365, 432–433.

Primary Examiner—Shep K. Rose
Attorney, Agent, or Firm—Robert L. Stone; Murray M. Grill; Herbert S. Sylvester

[57] ABSTRACT

A dental cream is disclosed having a two-tone flavor comprising essential oil and water-insoluble oleoresin extract of dried fruit, which oleoresin has higher sensation effect than said essential oil and is soluble in the said essential oil, the said flavor composition comprising about 0.01–5% by weight of the said aqueous oral composition, the said oleoresin comprising about 0.001–0.1% by weight of the said aqueous oral composition and the weight ratio of the said essential oil to the said oleoresin being at least about 10:1.

11 Claims, No Drawings

FLAVORED AQUEOUS ORAL COMPOSITION

This invention relates to an aqueous oral composition containing a novel flavour composition. In particular, the flavour composition comprises an essential oil and a high sensation water-insoluble oleoresin soluble in the said essential oil.

Aqueous oral compositions such as dental creams and mouthwashes have been prepared and sold in the past in which essential oil flavour is initially modified with chloroform as a high sensation ingredient. However, the effect of chloroform is limited by statute in several countries as to how much can be used and by its volatility.

It is an advantage of this invention that an aqueous oral composition is provided having a two-tone flavour effect; more specifically, initially an effect of essential oil flavour particularly during brushing, followed by blending with a high sensation flavour from an oleoresin extract of a dried fruit.

Further advantages will be apparent from consideration of the following specification.

According to the present invention an aqueous oral composition comprises an aqueous liquid vehicle having dispersed therein a flavour composition comprising essential oil and water-insoluble oleoresin extract of dried fruit, which oleoresin has higher sensation effect than the said essential oil and is soluble in the said essential oil, the flavour composition comprising about 0.01–5% by weight of the aqueous oral composition, the oleoresin comprising about 0.001–0.1% by weight of the aqueous oral composition and the weight ratio of the essential oil to the oleoresin being at least about 10:1.

The invention also extends to a process of preparing a two tone high sensation aqueous oral composition substantially as specifically described herein with reference to the Examples.

In the present invention the term "essential oil" includes oil from various parts of plants, such as the fruit, leaves, twigs or flowers, parts other than the fruit itself being preferred. Further, the term includes natural derivatives of such essential oils such as menthol, anethol, eucalyptol, carvone, eugenol, isoeugenol, terpenols, terpenes, terpinenes, and terpinones as well as synthetic materials similar to the natural materials and derivatives such as synthetic clove, cinnamic aldehyde, synthetic menthol and methyl salicylate. Typical essential oils are peppermint oil, spearmint oil, clove oil, sassafras oil, aniseed oil, cinnamon oil (including oil of cinnamon leaf and of cinnamon bark), eucalyptus oil, wintergreen oil, cassia oil, cardamon seed oil, orris oil, rose oil, geranium oil and thyme oil. Mixtures may be used. A preferred essential oil is a mixture of menthol, anethol and eucalyptus oil, typically in amounts of about 35–45% by weight of menthol, about 20–30% by weight of anethol and about 30–40% by weight of eucalyptus oil.

High sensation oleoresins used in accordance with the present invention are water-insoluble but soluble in the essential oil. Their sensation effect is greater than that of the essential oil with regard to taste, feeling and aroma. They are obtained by extraction from dried fruit. They are often viscous, pasty materials which remain after removal of solvent. The oleoresin Handbook, Fritzsche, Dodge and Olcott, Inc. New York, 2nd Edition, May 1974, describes many oleoresins, their properties and uses. The oleoresins described in the Handbook include Allspice Pimenta, Anise, Basil, Capsicum, Caraway, Cardamon, Celery, Cinnamon, Clove, Coriander, Cubeb, Cumin, Dill Seed, Fennel, Garlic, Ginger, Laurel Leaf, Mace, Marjoram, Mushroom, Mustard, Nutmeg, Onion, Origanum, Paprika, Parsley, Pepper, Rosemary, Sage Dalmatian, Tarragon, Thyme, Tumeric and Vanilla.

Typical oleoresins which provide high sensation are of the capsicum variety type from dried ripe fruits including capsicum oleoresin, and red pepper oleoresin. The specific capsicum oleoresin is obtained by solvent extraction from the dried ripe fruit of capsicum frutescens L. (chiles) or capsicum annum L. (Spanish pepper). Red pepper oleoresin is obtained by solvent extraction from the dried fruits of capsicum annum L. var. longum Sendt or the hybrid Louisiana Sport Pepper. After extraction the solvent is removed. (see Fenaroli's Handbook of Flavour Ingredients, Second Edition, Vol. 1, CRC Press, Cleveland, Ohio, U.S.A., 1975 (pages 304–305)).

A further example of a high sensation oleoresin suitable for the present invention is ginger. Ginger oleoresin is obtained by solvent extraction from dried rhizomes (zingiber officinale) followed by removal of solvent. (See Fenaroli's Handbook, supra, pages 364–365).

Black pepper oleoresin is also a suitable high sensation material. It is obtained by solvent extraction from dried unripe berries (piper nigrum) followed by removal of solvent (See Fenaroli's Handbook, supra pages 432–433). Other oleoresins such as cubeb oleoresins, and cumin oleoresin also may be used.

Further high sensation oleoresins of more moderate pungency than those mentioned above, such as celery seed oleoresin, clove bud oleoresin, curcuma oleoresin and lorage oleoresin may also be used.

The flavour composition comprises about 0.01–5% by weight, preferably about 0.5–1.5% by weight of the aqueous oral composition. The oleoresin comprises about 0.001–0.1% by weight of the aqueous oral composition, preferably about 0.002 to 0.075% and most preferably about 0.005–0.01%, the weight ratio of the essential oil to the oleoresin being at least about 10:1 and preferably about 100:1 to 200:1. For instance, when the aqueous oral composition contains 1% of essential oil, about 0.005–0.01% of oleoresin is preferably present.

The flavour composition is effective to provide the dental cream or mouthwash user with a two-tone effect; first the flavour sensation of the essential oil followed by the higher sensation effect of the oleoresin which is most keenly felt after the dental cream or mouthwash is removed from the oral cavity by rinsing. Since the dental cream or mouthwash may also include a material which promotes oral hygiene and continues to be effective well after removal of the dental cream or mouthwash from the oral cavity, the high flavour sensation oleoresin is effective to remind the user of the hygenic benefit.

It is noteworthy that capsicum oleoresin has been reported as having been used in chewing gum in amount of 46 ppm, that is 0.0046% (Fenaroli's Handbook, supra, pages 305–306). Such chewing gum would be expected to contain additional flavouring agent since the flavour tone of capsicum oleoresin is too pungent to be desirable as a sole flavouring ingredient in a chewing gum. However, the high sensation effect of the capsicum oleoresin from a chewing gum, particularly after removal of the chewing gum from the mouth would be substantially less than in a dental cream since the mastication of the gum is intended to continue while the flavour is present. Thus, substantial removal of the capsicum oleoresin from a chewing gum would occur before the chewing gum is removed from the mouth. In an aqueous oral composition such as a dental cream or a mouthwash the note from the capsicum oleoresin is optimized by its exercising its high sensation effect well after removal of the dental cream from the oral cavity.

Powdered ginger is disclosed in U.S. Pat. No. 1,386,282 as a dentifrice additive in amount of 20 parts in a dentifrice of 524.6 parts (about 3.8%). Such a level would be too pungent for commercial usefulness if ginger oleoresin had been used. Ginger is also disclosed as a toothpaste additive in British Pat. No. 1,438,205 in amount of 0.2%, with 1% menthol also being present. This level of ginger and the 5:1 ratio of menthol as essential oil to ginger, would provide a product too pungent for commercial use if ginger oleoresin had been used.

In the preparation of a dental cream in accordance with the present invention the oleoresin extract is dissolved in the essential oil and dispersed in the dental cream vehicle which contains water, a humectant or more preferably mixtures thereof together with a solid phase including gelling agent. Polishing agent is dispersed in this product. The flavour composition may be added with a portion of the polishing material or later, after deaeration. The product has a gel or creamy consistency with a viscosity such that it is extrudible from an aerosol container or a collapsible tube (for instance lined lead, lined or unlined aluminium or plastic).

In the preparation of a mouthwash of the present invention the oleoresin extract is dissolved in the essential oil and dispersed in the mouthwash vehicle which contains water, preferably with a humectant and a non-toxic alcohol such as ethanol.

In general, the liquids in a dental cream or mouthwash in accordance with the invention will comprise chiefly water, typically with a humectant such as glycerine, aqueous solutions of sorbitol, propylene glycol, and polyethylene glycol 400, including suitable mixtures thereof. A non-toxic alcohol such as ethanol may be present too, particularly in a mouthwash. It is advantageous usually to use a mixture of both water and a humectant or binder such as glycerine or sorbitol. The total liquid content will generally be about 20 to 75 percent by weight of the formulation. It is preferred to use also a gelling agent in dental creams and gels such as the natural and synthetic gums and gum like materials, for example, Irish moss, gum tragacanth, methyl cellulose, polyvinylpyrrolidone, hydrophilic colloidal carboxyvinyl polymers, such as those sold under the trademark Carbopol 934 and 940 and synthetic silicated clays such as those sold under the trademark Laponite CP and Laponite SP. These grades of Laponite have the formula

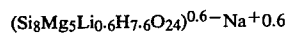

$(Si_8Mg_5Li_{0.6}H_{7.6}O_{24})^{0.6-} Na^+{0.6}$

The solid portion of the vehicle is usually present in an amount of up to about 10 percent preferably about 0.2 to 5 percent by weight of the formulation.

The dental cream formulations will generally also include a dentally acceptable, substantially water insoluble, polishing agent of the type commonly employed in dental creams. Representative polishing agents include, for example, dicalcium phosphate, tricalcium phosphate, insoluble sodium metaphosphate, aluminium hydroxide, including hydrated alumina, colloidal silica, magnesium carbonate, calcium carbonate, calcium pyrophosphate, and bentonite, including suitable mixtures thereof. When employed, it is preferred to use the water insoluble phosphate salts as the polishing agent and more particularly insoluble sodium metaphosphate and/or a calcium phosphate such as dicalcium phosphate dihydrate. When the dental cream is a visually clear gel or opacified gel, a polishing agent of colloidal silica, such as those sold under the trademark Syloid as Syloid 72 and Syloid 74 or under the trademark Santocel as Santocel 100 and synthetic alkali metal aluminosilicate complexes (including silica containing combined alumina) may be particularly useful. They have refractive indices close to the refractive indices of gelling agents-liquid systems commonly used in dentifrices (which generally include humectants such as glycerine and sorbitol). When employed, the total polishing agent content is generally in amounts from about 15 to 75 percent by weight in a dental cream.

Organic surface-active agents are used in the composition of the present invention to assist in achieving thorough and complete dispersion of the compositions of the present invention throughout the oral cavity and render the said compositions more cosmetically acceptable. The organic surface-active agent material may be anionic, nonionic, ampholytic, or cationic in nature, and it is preferred to employ as the surface-active agent a detersive material which imparts to the composition detersive and foaming properties. Suitable such detergents are water-soluble salts of higher fatty acid monoglyceride monosulphates, such as the sodium salt of the monosulphated monoglyceride of hydrogenated coconut oil fatty acids, higher alkyl sulphates, such as sodium lauryl sulphate, alkyl aryl sulphonates, such as sodium dodecyl benzene sulphonate, higher alkyl sulphoacetates, higher fatty acid esters of 1,2-dihydroxy propane sulphonates, olefin sulphonates and the substantially saturated higher aliphatic acyl amides of lower aliphatic amino carboxylic acid compounds, such as those having 12 to 16 carbon atoms in the fatty acid, or acyl radicals. Examples of the last mentioned amides are N-lauroyl sarcosine, and the sodium, potassium and ethanolamine salts of N-lauroyl, N-myristoyl, or N-palmitoyl sarcosine which should be substantially free from soap or similar higher fatty acid material which tends to substantially reduce the effect of these compounds. The use of these sarcosinate compounds is particularly advantageous since these materials exhibit a prolonged and marked effect in the inhibition of acid formation in the oral cavity due to breakdown of carbohydrates in addition to exerting some reduction in the solubility of tooth enamel in acid solutions.

Other particularly suitable surface active materials include nonionic agents such as condensates of sorbitan monostearate with approximately 20 moles of ethylene oxide, condensates of ethylene oxide with propylene oxide, condensates of propylene glycol ("Pluronics"), and amphoteric agents such as quaternized imidazole derivatives which are available under the trademark "Miranol" such as Miranol C₂M.

Other suitable nonionic detergents are the condensation products of an α-olefin oxide containing 10 to 20 carbon atoms, a polyhydric alcohol containing 2 to 10 carbons and 2 to 6 hydroxyl groups and either ethylene oxide or a heteric mixture of ethylene oxide and propylene oxide. The resultant detergents are heteric polymers having a molecular weight in the range of 400 to about 1600 and containing 40% to 80% by weight of ethylene oxide, with an α-olefin oxide to polyhydric alcohol mole ratio in the range of about 1:1 to 1:3. These detergents are manufactured using well-known polymerization techniques under conditions of high temperature and high pressure. The olefin oxide and polyhydric alcohol usually are added to the reactor prior to the addition of ethylene oxide. These nonionic detergents may be mixed with similar nonionic detergents as well as other types of nonionic detergents described herein.

It is preferred to use from about 0.05 to 5% by weight of the foregoing surface-active materials in the oral preparations of the present invention.

Various other materials may be incorporated in the oral compositions of this invention. Examples thereof are colouring or whitening agents or dyestuffs, preservatives, silicones, chlorophyll compounds, ammoniated materials such as urea, diammonium phosphate and mixtures thereof, and other constituents. These adjuvants are incorporated in the compositions of the present invention in amounts which do not substantially adversely affect the properties and characteristics desired and are selected and used in proper amount depending upon the particular type of preparation involved.

The compositions of the present invention may also contain a fluorine-containing compound having a beneficial effect on the care and hygiene of the oral cavity, e.g., diminution of enamel solubility in acid and protection of the teeth against decay. Examples thereof include sodium fluoride, stannous fluoride, potassium fluoride, potassium stannous fluoride ($SnF_2KF$), potassium fluorozirconate, sodium hexafluorostannate, stannous chlorofluoride, and sodium monofluorophosphate. These materials which dissociate or release fluorine-containing ions, suitably may be present in an effective but non-toxic amount usually within the range of about 0.1 to 1% by weight, based on the water soluble fluorine content thereof. Sodium fluoride, stannous fluoride, and sodium monofluorophosphate are particularly preferred, as well as mixtures thereof.

Antibacterial agents may also be employed in the oral preparations of the present invention to provide a total content of such agents of up to about 5% by weight, preferably 0.01 to 5.0%, most preferably about 0.05 to 1.0%. Typical antibacterial agents include:
Benzethonium chloride
$N^1$-(4-chlorobenzyl)-$N^5$-(2,4-dichlorobenzyl)biguanide;
p-chlorophenyl biguanide;
4-chlorobenzhydryl biguanide;
4-chlorobenzhydrylguanylurea;
N-3-lauroxpropyl-$N^5$-p-chlorobenzylbiguanide;
1-(lauryldimethylammonium)-8-(p-chlorobenzyldimethylammonium)octane dichloride;
5,6-dichloro-2-guanidinobenzimidazole;
$N^1$-p-chlorophenyl-$N^5$-laurylbiguanide;
1,6-di-p-chlorophenyl biguanidohexane;
1,6-bis(2-ethylhexyl biguanido)hexane;
5-amino-1,3-bis(2-ethylhexyl)-5-methylhexahydropyrimidine;
and their non-toxic acid addition salts.

Other agents which promote oral hygiene such as anticalculus agents (e.g. ethylene diamine tetramethyl phosphonic acid or salts thereof) may also be used; typically in amounts up to about 15% by weight.

Synthetic finely divided pyrogenic silica such as those sold under the trademark Cab-O-Sil M-5, Syloid 244, Syloid 266 and Aerosil D-200 may also be employed in amounts of about 1-5% by weight to promote thickening or gelling and to improve clarity of the dentifrice.

In addition to the flavour components of the dental cream of the present invention, sweetening agents may also be present. Suitable sweetening agents include sucrose, lactose, maltose, sorbitol, sodium cyclamate and sodium saccharine. The sweetening agent may be present in amount of at least about 0.01% by weight. The total amount of sialogogue, including flavour composition and sweetening agent is up to about 5% by weight of the dental cream.

It is desirable to adjust the pH of the dental cream formulations to the range of about 3 to 10 using such acids as citric, acetic, chloropropionic, malonic, formic, fumaric, methoxyacetic, and propionic, or salts thereof or bases such as of sodium hydroxide.

The invention may be put into practice in various ways and a number of specific embodiments will be described to illustrate the invention with reference to the accompanying Examples. Dental cream formulations are prepared in the usual manner, except as indicated, and all amounts and proportions are by weight except as otherwise indicated.

EXAMPLE 1

0.01 part of capsicum oleoresin was dissolved in 1 part of an essential oil containing about two-fifths menthol, about one-quarter anethol and about one-third eucalyptus oil. The 1.01 parts of flavour composition thereby formed was dispersed in a dental cream vehicle containing 25 parts of glycerine and 39.620 parts of water which also contained 0.2 parts of sodium saccharine and 0.5 parts of sodium benzoate. The dental cream vehicle also contained a solid phase of 1.1 parts of sodium carboxymethyl cellulose, 27 parts of silica containing about 1% combined alumina, 0.4 parts of titanium dioxide, 2.57 parts of ethylene diamine tetramethyl phosphonic acid (EDITEMPA), 1.5 parts of sodium lauryl sulphate and 0.92 parts of sodium hydroxide to adjust the pH and neutralise the EDITEMPA.

When this dental cream was dispersed in the mouth during toothbrushing the flavour of the menthol-anethol-eucalyptus oil was initially felt. By the time the dental cream was rinsed from the mouth, the first flavour tone was supplemented by the high sensation separate flavour tone of capsicum oleoresin which remained well after removal of the dental cream from the mouth.

EXAMPLES 2 AND 3

A similar high sensation flavour tone as in Example 1 was experienced after rinsing the oral cavity free of dental cream when 0.005 (Example 2), and 0.05 parts (Example 3) of capsicum oleoresin were employed in the dental cream with minor adjustment in the amount of water.

EXAMPLE 4

Another high sensation flavour tone was experienced after rinsing the oral cavity free of dental cream when ginger oleoresin is used in place of capsicum oleoresin in the dental cream of Example 1.

EXAMPLE 5

A further high sensation flavour tone was experienced after rinsing the oral cavity free of dental cream when black pepper oleoresin was used in place of capsicum oleoresin in the dental cream of Example 1.

EXAMPLES 6A, 6B AND 6C

The following high sensation mouthwashes were prepared:

| COMPONENTS | PARTS A | B | C |
|---|---|---|---|
| Ethanol (95%) | 6.000 | 6.000 | 6.000 |
| Benzethonium chloride | 0.082 | — | — |
| Glycerine | 10.130 | 10.130 | 10.130 |
| Essential oil of Example 1 | 0.218 | 0.218 | 0.218 |
| Capsicum oleoresin | 0.075 | 0.075 | 0.010 |
| Sorbitan monstearate condensate with 20 moles of polyethylene oxide | 2.000 | 2.000 | 2.000 |
| Water | 81.371 | 81.453 | 81.518 |
| Red colour (1% solution) | 0.100 | 0.100 | 0.100 |

We claim:

1. An aqueous oral composition comprising an aqueous liquid dental cream or mouthwash vehicle having dispersed therein a two-tone flavour composition comprising essential oil and water-insoluble oleoresin extract of dried fruit, which oleoresin has higher sensation effect than said essential oil and is soluble in the said essential oil, the said flavour composition comprising about 0.01-5% by weight of the said aqueous oral composition, the said oleoresin comprising about 0.001-0.1% by weight of the said aqueous oral composition and the weight ratio of the said essential oil to the said oleoresin being at least about 10:1.

2. The aqueous oral composition as claimed in claim 1 in which the essential oil contains at least one of menthol, anethol and eucalyptus oil.

3. The aqueous oral composition as claimed in claim 1 in which the oleoresin is selected from the group consisting of capsicum oleoresin, red pepper oleoresin, ginger oleoresin and black pepper oleoresin.

4. The aqueous oral composition as claimed in claim 3 in which the oleoresin is capsicum oleoresin.

5. The aqueous oral composition as claimed in claim 1 in which the flavour composition comprises about 0.5-1.5% by weight of the aqueous oral composition.

6. The aqueous oral composition as claimed in claim 1 in which the weight ratio of essential oil to said oleoresin is about 100:1 to 200:1.

7. The aqueous oral composition as claimed in claim 6 in which the flavour composition comprises about 0.5-1.5% by weight of the aqueous oral composition and the oleoresin comprises about 0.005-0.01% by weight of the said aqueous oral composition.

8. An aqueous oral composition as claimed in claim 1 in the form of a dental cream.

9. The dental cream as claimed in claim 8 in which the aqueous liquid vehicle contains a humectant and which contains a dentally acceptable substantially water-insoluble polishing agent.

10. An aqueous oral composition as claimed in claim 1 in the form of a mouthwash.

11. The mouthwash as claimed in claim 1 in which a humectant and a non-toxic alcohol are present in the liquid vehicle.

* * * * *